US005618565A

United States Patent [19]
Thomas

[11] Patent Number: 5,618,565
[45] Date of Patent: Apr. 8, 1997

[54] COMPOSITION FOR EXTERMINATING FIRE ANTS

[76] Inventor: Michael H. Thomas, Rte. 3, 193-1, Espanola, N.M. 87532

[21] Appl. No.: 531,237

[22] Filed: Sep. 19, 1995

[51] Int. Cl.⁶ ............................ A01N 59/00; A01N 65/00
[52] U.S. Cl. ..................... 424/717; 424/84; 424/195.1; 514/918; 514/920
[58] Field of Search ......................... 424/84, 195.1, 424/717; 514/920, 918

[56] References Cited

U.S. PATENT DOCUMENTS 4,455,304  6/1984  Yaralian ........................... 424/195.1

Primary Examiner—John Pak
Attorney, Agent, or Firm—Samuel M. Freund

[57] ABSTRACT

A composition of matter for exterminating fire ants. A dry powder composition of matter which consists essentially of sodium bicarbonate, a powdered acid, an ant attractant, and a deterrent for animals, birds and insects other than fire ants, such as red chili powder or capsaicin, has been found to selectively kill fire ants, once eaten by the ants or taken into a warm, moist ant mound. The composition does not harm humans, cattle, horses, birds, rodents, etc., and also will not harm black, red, or sugar ants.

2 Claims, No Drawings

COMPOSITION FOR EXTERMINATING FIRE ANTS

FIELD OF THE INVENTION

The present invention relates generally to insect extermination and, more particularly, to the selective extermination of fire ants.

BACKGROUND OF THE INVENTION

Fire ants have become well-established throughout the southern United States, from Florida to Texas. They damage natural ecosystems, drive out other species and cause billions of dollars in damage to farms and ranches, to pastures and prairies, and in cities. See, e.g. Albuquerque Journal, Section E, page 9, May 28, 1995. Although research by the Department of Agriculture may provide an environmentally acceptable control for this problem in the future, presently only non-specific chemicals appear to be effective against fire ants. Unfortunately, in addition to the fire ants, most other wildlife bas been killed in the treatment areas. See, e.g., Time, page 5, Jun. 5, 1995. Moreover, the presence of multiple queens in fire ant mounds has further confounded chemical control. See, Albuquerque Journal, *supra*.

The use of capsaicins is known for repelling rodents. See, e g., "Coating Materials Containing Rodent Repellents," by Kenji Nagata et al., Japanese Patent No. JP 93-29754 930125, and "Poly(vinyl chloride) Containing Rodent Repellents in Manufacturing Electrical Cable Covering," by Emiko Fujita, Japanese Patent No. JP 92-98341 920417.

Sodium bicarbonate and sodium pyrophosphate mixtures, with powdered milk or other food material as an insect attractant, have been used to kill cockroaches and other insects having a hard shell carapace, such as cockroaches and locusts. See, e.g., "Sodium Bicarbonate-Containing Insecticidal Bait," by Ganni Gianfranceschi et al., European Patent No. EP 90-420292 900621, and "Composition For Destroying Insects Having Hard Carapace, e.g. Locust-Containing Food Material And Agent Which Swells On Ingestion, Causing Body To Burst," by R. E. Booker et al., European Patent. No. EP 462347 A 911227. No mention is made in these latter two references of the use of a repellent for other species, nor is there any teaching therein that the described compositions are effective against insects not having hard carapaces of chitin, such as ants.

Baking powders are well-known compositions use in place of leavening or fermentation agents to make light, flour-based baking products. Sodium bicarbonate ("baking soda"), is universally used to produce the carbon dioxide evolved when the powder is thoroughly moistened and heated. To supply the acid for the reaction, three classes of materials are in common use: (1) potassium hydrogen tartrate ("cream of tartar"), and less frequently, tartaric acid; (2) calcium dihydrogen phosphate (calcium monophosphate); and (3) sodium aluminum sulfate. Starch is usually added to diminish the effect of moisture in storage. The proportions are also well-known, except that there is some variation, since it is customary to use some excess of carbonate. Alum-containing baking powders react slowly at room temperature, phosphate baking powders react at medium speed, and tartrate baking powders act quickly to produce carbon dioxide.

Accordingly, it is an object of the present invention of provide a composition of matter for selectively exterminating fire ants.

Another object of the invention is to provide a non-poisonous composition of matter for selectively exterminating fire ants.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the composition of matter for selectively killing fire ants hereof consists essentially of a dry powder mixture of sodium bicarbonate, an attractant for ants, and a deterrent for animals, birds and other insects.

It is preferred that the dry powder include a powdered acid such that carbon dioxide is generated when the composition is moistened.

It is also preferred that the attractant for ants include corn starch.

Preferably, the deterrent for animals, birds and other insects includes red chili powder and/or capsaicin.

Benefits and advantages of the present invention include great effectiveness against fire ants, their eggs and queens, while having no effect on animals, birds and black, red or sugar ants.

DETAILED DESCRIPTION OF THE PREFERRED EMBODIMENTS OF THE INVENTION

Briefly, the present, invention includes a dry powder composition of matter which consists essentially of a mixture of sodium bicarbonate, an ant attractant, and a deterrent for animals, birds and insects other than fire ants. Red chili powder or capsaicin have been successfully used to achieve the latter function. Preferably, a powdered acid is included such that carbon dioxide is evolved when the composition is moistened. Preferably also, corn starch is used for the ant attractant. The composition has been found to selectively kill fire ants, once eaten by the ants, or taken into a warm, moist mound thereby. As understood by the inventor, in the former case, carbon dioxide is rapidly formed in the ingesting ant, causing the ant to explode. Since sodium bicarbonate alone will generate carbon dioxide by reaction thereof with the stomach acid of an ant, if solely individuals ingesting ants are to be exterminated, only sodium bicarbonate need be mixed with starch or another ant attractant and a deterrent for all but fire ants. In the latter situation, carbon dioxide is formed within the mound, thereby asphyxiating the ants, their eggs, and any queens inhabiting the mound. The corn starch is used as a carrier for the carbon dioxide-generating ingredients of the composition, and assists in keeping the mixture in powdered form, while the red chili powder or capsaicin repels all but the fire ants. The corn starch also attracts the fire ants to ingest the composition and to carry the composition into their mounds for later consumption.

It has been found that 1–2 cups of the present dry powder composition of matter is effective in destroying all of the fire ants in a given mound. The choice of chemical components is environmentally safe, having a near neutral pH, and will actually enrich the soil remaining after the fire ant colony has been destroyed. The composition has been found to be harmless to lawns.

Either red chili powder or capsaicin is added to commercially available baking powder at 1–2 Oz. thereof to three pounds of the baking powder, and the resulting powder thoroughly mixed to form one composition of the present invention. The concentration of active or carbon dioxide generating materials may be varied from 15 to 45 weight percent of the composition by increasing the sodium bicarbonate and sodium pyrophosphate levels. Increasing the concentration of these compounds increases the killing capacity of the material for fire ants. A mixture of ant attractant such as corn starch, sodium bicarbonate, and capsaicin or red chili powder also effective for killing ingesting fire ants, may consist essentially of 25–30% by weight of starch or other ant attractant, 2–4% by corn weight of capsaicin or red chili powder and the remainder sodium bicarbonate.

A composition of matter found to work effectively consisted essentially of a dry mixture of baking powder and 2–4 weight percent of capsaicin or red chili powder, where the baking powder included 30–40 weight percent of sodium acid pyrophosphate, 30–35 weight percent of sodium bicarbonate, 25–30 weight percent of corn starch, and 3–8 weight percent of monocalcium phosphate.

The foregoing description of several preferred embodiments of the invention has been presented for purposes of illustration and description. It is not intended to be exhaustive or to limit the invention to the precise form disclosed, and obviously many modifications and variations are possible in light of the above teaching. For example, it would be apparent to one having skill in the art of insect eradication after having studied the present disclosure, that other deterrent materials may be employed. Moreover, other ant attractants may be utilized, such as powdered milk. In fact, chemical attractants having no food value are also envisioned. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A dry powder composition of matter for killing fire ants which consists essentially of sodium bicarbonate, an ant attractant, and red chili powder.

2. A dry powder composition of matter for killing fire ants which consists essentially of baking powder and 2 to 4 weight percent of red chili powder.

* * * * *